United States Patent [19]

Ebizawa et al.

[11] Patent Number: 4,507,191
[45] Date of Patent: Mar. 26, 1985

[54] OXYGEN SENSOR WITH HEATER

[75] Inventors: Akio Ebizawa, Iwakura; Kazuo Taguchi, Nagoya; Toshio Okumura, Kagamihara, all of Japan

[73] Assignee: NGK Spark Plug Co., Ltd., Nagoya, Japan

[21] Appl. No.: 545,180

[22] Filed: Oct. 25, 1983

[30] Foreign Application Priority Data

Nov. 17, 1982 [JP] Japan .................. 57-200443

[51] Int. Cl.³ ........................................... G01N 27/58
[52] U.S. Cl. ..................................... 204/427; 204/408
[58] Field of Search ............. 204/408, 421, 424, 425, 204/427, 428; 219/543, 544, 553

[56] References Cited

U.S. PATENT DOCUMENTS

| | | | |
|---|---|---|---|
| 3,622,755 | 11/1971 | Vedder | 219/553 X |
| 4,035,613 | 7/1977 | Sagawa et al. | 219/543 X |
| 4,178,222 | 12/1979 | Murphy et al. | 204/408 X |
| 4,212,720 | 7/1980 | Maurer et al. | 204/424 |
| 4,219,399 | 8/1980 | Gruner et al. | 204/408 |
| 4,234,786 | 11/1980 | Borom et al. | 219/544 |
| 4,283,703 | 8/1981 | Horwitt | 204/427 X |
| 4,357,526 | 11/1982 | Yamamoto et al. | 219/544 |

Primary Examiner—G. L. Kaplan
Assistant Examiner—Nam X. Nguyen
Attorney, Agent, or Firm—Wegner & Bretschneider

[57] ABSTRACT

A heater-incorporating oxygen sensor includes a solid electrolyte oxygen sensor element comprising a solid electrolyte provided with electrodes on both its sides and a heater, said heater being a ceramic heater formed by sintering and embedding a metallized pattern in a ceramic insulator as one solid body, said ceramic heater being disposed within a space surrounded with said oxygen sensor element.

2 Claims, 9 Drawing Figures

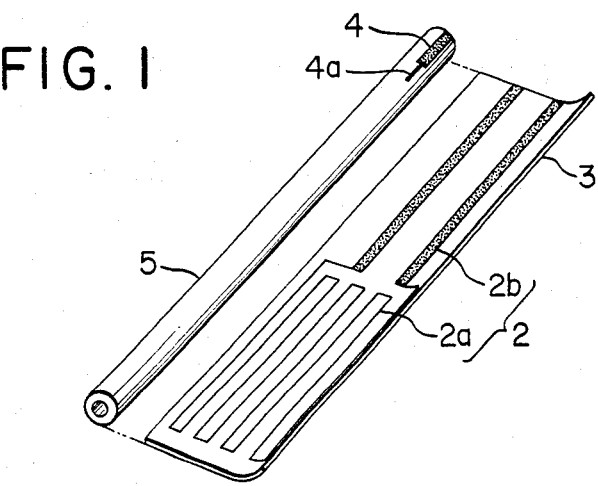
FIG. 1
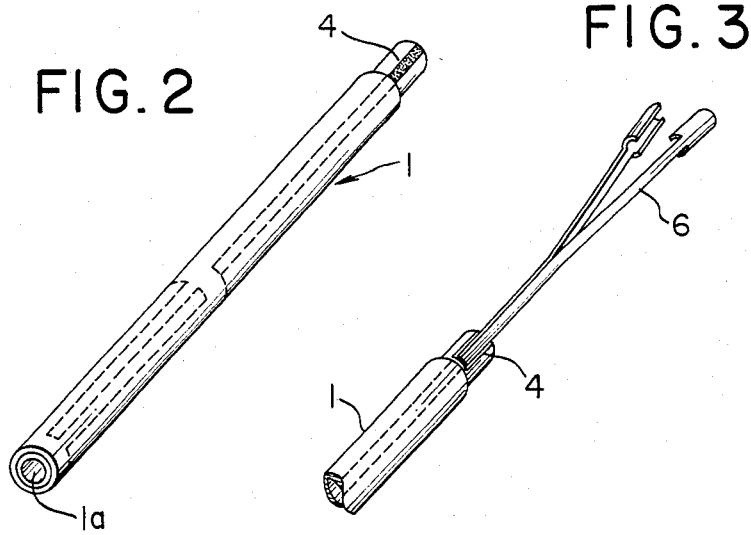
FIG. 2
FIG. 3

OXYGEN SENSOR WITH HEATER

FIELD OF THE INVENTION

The present invention relates to a solid electrolyte oxygen sensor of the heating type, and more particularly to such a sensor including a heater for said sensor.

BACKGROUND OF THE INVENTION

Solid electrolyte oxygen sensors include as a sensor element oxygen ion-conductive solid electrolyte (usually a sintered body), which is ordinarily provided on both its sides with porous electrodes. When the respective electrodes are exposed to a reference oxygen source (usually air) and an object to be measured, there is an electric potential difference in response to a difference in the partial oxygen pressure between both electrodes. The potential difference is guided to terminals where it is detected.

The sensors of this type are used especially for the measurement of oxygen (or an unburnt combustible matter) in exhaust gases discharged from internal combustion engines such as those for automobiles. The solid electrolyte used for that purpose includes those based on zirconia, hafnia or the like; however, they can work only in high-temperatures of about 400 degrees C. or higher, and their working temperature tends to rise further with the lapse of time during use. For this reason, when the temperature of exhaust gases is low, the sensor does not function well. For example, Japanese Patent Kokai Publication No. 55(1980)-69048 teaches an assembly wherein a ceramic insulating tube having a heating coil attached to one end is inserted into the inner bottom of a solid electrolyte element in the form of a bottomed cylinder, or a modification of such an assembly which further includes a heater arranged around that element.

In the conventional heater-incorporating oxygen sensors as mentioned above, however, a separately prepared, small-sized heater is merely attached to the end portion of the element, so that the overall structure of the sensor is complicated (provision of a heater-supporting structure or protective insulator such as an insulating tube, special leads and assembling means) with an increased number of assembling steps. This leads to increased production cost. It is further noted that, when the heater is mounted on the outside of the element, there are certain deteriorations of the heater.

SUMMARY OF THE INVENTION

A main object of the present invention is to provide a solid electrolyte oxygen sensor which is substantially free from the above-mentioned drawbacks of the prior art, works in a stable manner, and is of a simpler but firm structure that suppresses the generation of thermal stress, which would otherwise cause loosening of the sensor arrangement and, eventually, lead to breakage thereof.

Another object of the present invention is to provide a heater-incorporating oxygen sensor which takes a lesser space or room, is formed from smaller amounts of materials or members, and produces the desired effect with less electric current.

With these objects in mind, the present invention provides an solid electrolyte oxygen sensor including an oxygen sensor element comprising a solid electrolyte provided with electrodes on both its sides and a heater, in which said heater is formed of a metal pattern embedded in a ceramic insulator as one solid body, and disposed within a space surrounded with said oxygen sensor element.

BRIEF DESCRIPTION OF THE DRAWINGS

The aforesaid and other objects and features of the present invention will become apparent from the following detailed description with reference to the accompanying drawings, in which:

FIGS. 1 to 3 show together one embodiment of the ceramic heater according to the present invention, FIG. 1 being a view showing an exploded green sheet prior to winding.

FIG. 6 is an end view taken along the line VI—VI of FIG. 5;

FIG. 7 shows another embodiment corresponding to FIG. 5;

DETAILED DESCRIPTION OF THE PREFERRED EMBODIMENTS OF THE INVENTION

Figure 4:
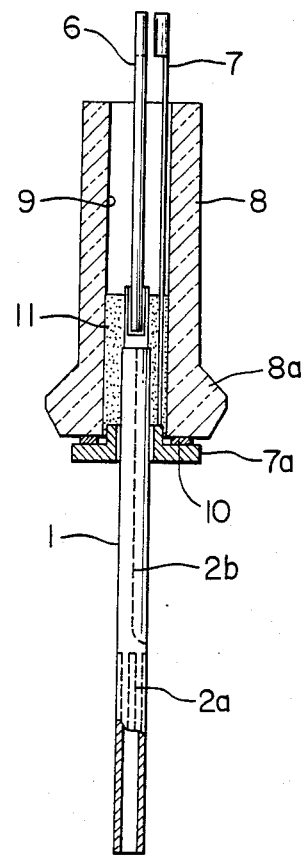
FIG. 4 is a view showing an intermediate arrangement comprising the ceramic heater attached to an insulator.

The oxygen sensor element is preferably in the form of a bottomed cylinder, but may assume another shape, such as a semicircular shape, if required.

The ceramic heater is formed by sintering and embedding a metallized pattern in a cylindrical or columnar ceramic insulator (such as an insulating tube) as one piece. When an insulating tube is used as the ceramic insulator as an example, a green ceramic sheet onto which a metallized paste pattern is formed preferably by printing, is wound around the bonded to an insulating tube blank prior to sintering. The resulting composite is then sintered together to obtain a cylindrical ceramic heater. Formation of the metallized pattern onto one end of the insulating tube may usually suffice for the purpose of the present invention. Alternatively, a patterned, green ceramic sheet may be wound around a sintered insulating tube, followed by re-sintering. Furthermore, after pattern formation on an insulating tube, a green sheet may be wound around the patterned insulating tube, followed by sintering.

As the metal paste, heat-resistant paste should preferably be selected from the known metal pastes for metallized patterning. To this end, for instance, high melting metals such as W and/or Mo, or platinum may be used.

The ceramic heater is bonded and fixed, together with a lead for the inner electrode, to the inside (usually the inner wall of a centerbore) of an insulator (usually a ceramic insulator) previously disposed adjacent to the open end of the oxygen sensor element (hereinafter referred to "element") with the use of bonding agents based on heat-resistant bonding inorganic materials, i.e, ceramic bonding materials. The heat-resistant ceramic bonding agents may be those resistant to at least 700 degrees C., encompassing phosphate cement, silicon compound or bonding agents composed mainly of inorand outer surfaces. The inner electrode extends to the upper end face of the element 21 where a terminal portion 21d is defined, while the outer electrode extends to the collar portion 21e where a terminal portion 21c is defined. The terminal portions 21d and 21c are electrically connected with the terminal 7a for the element through a packing 12 and with the main metal part 22 (for grounding) through a packing 13, respectively.

The upper inner bore portion in the main metal body 22 is formed by a large-diameter portion 22b adapted to receive the lower large-diameter portion 8a of the ceramic insulator 8. An upper cylindrical housing 24 is forcibly engaged with the bent caulking portion 22c of the main metal body 22 through soft metals 14 and 15, and retained on the main metal body 22 under a downward force. In this case, heat is generated and concentrated at the thin central portion 22e of the main metal body 22 by the application of the known thermal caulking technique for the expansion thereof, whereby the insulator and the upper housing are assembled to the main metal body, and the terminal 7a is fixedly engaged with the upper end face of the element 21 through metal packings 10 and 12.

Through the upper housing 24 extends the ceramic insulator 8, through the centerbore in which the lead 7 and the connecting terminals 6 (although one terminal is clearly shown, two terminals are used) extend without contacting each other, and are connected with the associated external lead 7b and terminals 6a at the upper end thereof. The external leads 7b and 6a are retained within an upper protective cap 25 by a resilient (rubber, etc.) cap 26 (Teflon ®, ceramics, etc.). The cap 25 has its large-diameter portion 25 fitted into the upper portion of the housing 24 ventilated at its upper end, and fixed in place with a clearance by spot welding 26 or like means.

The upper end of the housing 24 is disposed with a given clearance with respect to the large-diameter portion 25a of the cap 25. Thus, a communication passageway from the bottom 21b of the centerbore 21a in the element 21 to the air is defined by the bore 1a in the ceramic heater 1, the upper terminal portion thereof, the inner bore 9 in the insulator, the upper end thereof and the clearance between the housing 24 and the cap 25.

Figure 5:
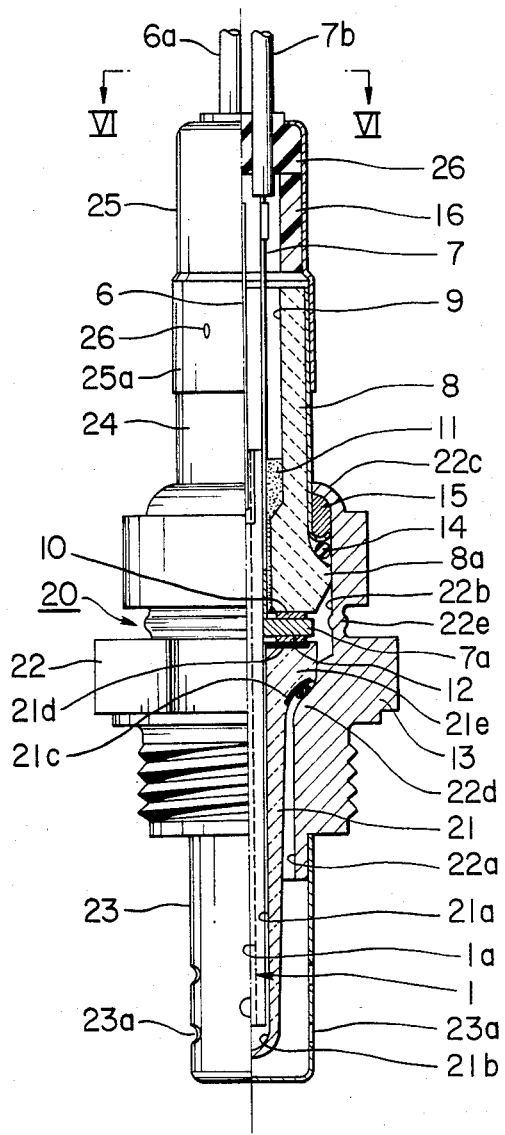
FIG. 5 is a view showing one embodiment of the oxygen sensor to which the intermediate arrangement of FIG. 4 is assembled.

FIG. 6 shows the upper end face of the sensor, as viewed from the direction of the line VI—VI of FIG. 5.

FIG. 7 shows another embodiment. This embodiment is generally similar to that of FIG. 5, except that a ceramic heater 1' in the form of a solid column is used, and a communication passageway leading to the air is modified correspondingly.

Figure 9:
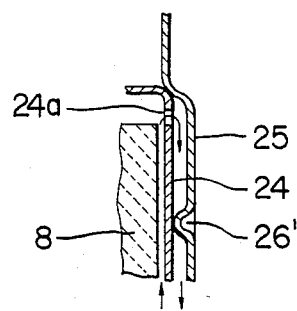
FIG. 9 is an enlarged view of a portion of FIG. 7 encircled with a chain line IX.

The lower terminal (ring-like portion) 7b of a lead 7' for the element is engaged with the upper terminal portion 21d of the element 21, and provided therein with a slit 7c in the radial direction, as illustrated in FIG. 9. Furthermore, the ring-like portion 7b of the terminal 7' is provided therearound with a sheet-like ring packing 10' having an associated slit 10a, and the inner periphery of the ring-like portion 7b is brought in close contact with the outer periphery of the ceramic heater 1'.

A heat-resistant bonding agent (heat-resistant cement such as silica cement) 11 covers the upper end of the ceramic heater 1', is charged in portions including the terminal 6 and an element lead 7', and fixes these to the insulator 8.

Between the outer periphery of the insulator 8 and the inner periphery of the housing 24, there is an air communication passageway defined by a given clearance (or a longitudinal groove or the like passage), which communicates with the air through the upper hole 24a in the housing 24, the outside of the housing 24 and the clearance between the inside of the cap 25 and the housing 24. In this case, the cap 25 is closely fitted (by caulking or like means) onto the upper edge of the housing 24. The air communication passageway extends from the lower end of the housing 24 through a slit (not shown) in a soft metal packing 14' and the outer periphery of the lower large-diameter portion 8a of the insulator, and communicates with the large-diameter portion 22b in the inner bore in the main metal body 22, where it communicates with the slit 7c formed in the terminal 7b opening in that portion.

The heat-resistant cement 11' should resist to a temperature of 500 degrees C. or higher, preferably 700 degrees C. or higher, since the foregoing that portion reaches at most 500 degrees C. or higher. (Thus, borosilicate- or boric acid-base cement having a softening point of about 800 degrees C. is used).

The cap 25 may be fixed to the housing 24 by spot caulking with a punch (or a clamp) 26'.

Figure 8:
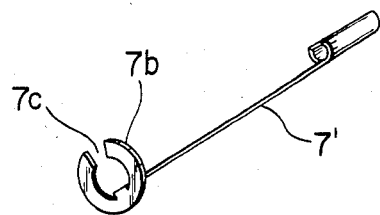
FIG. 8 shows one embodiment of a connecting terminal for the sensor element used in the embodiment of FIG. 7.

FIG. 8 is one example of the connecting terminal 7' for the element used in this embodiment, the ring-like end 7b of which is slitted at 7c.

It is noted that the protective cap 23 for the element 21 is fixed to the lower end of the main metal body 22 by a caulking member 22f.

As is the case with the first embodiment, for the purpose of assembling according to this embodiment, the ceramic heater 1 is previously bonded and fixed to the insulator 8 together with the leads 7, 7'. The resulting set is fixed, together with the element 21, to the main metal body 22 by thermal caulking.

FIG. 9 is an enlarged view of a portion indicated by IX in FIG. 7. The ceramic heater 1 is used as an example is in the form of a cylinder having an outer diameter of about 2.5 mm, an inner diameter of about 0.6 mm, a length of about 40 to 50 mm and a resistance value of about 5 ohms. However, the dimensions and resistance value may be changed depending upon the purpose.

In either embodiment, between the element 21 and the ceramic heater 1 or 1', there is a clearance for permitting the thermal expansion of the heater 1 or 1'. When a Mo paste is used, it is easy to obtain a ceramic heater including a resistor circuit of a desired pattern exhibiting constantly 5 ohms at 12 to 15 V. The thus obtained ceramic heater-incorporating oxygen sensor works well, even when the temperature of exhaust gases drops down to 300 degrees C., whereas, however, a sensor without heater already works in an instable manner.

While the present invention has been described with reference to the specific embodiments, it is understood that many changes and modifications may be made without departing from the scope as defined in the appended claims.

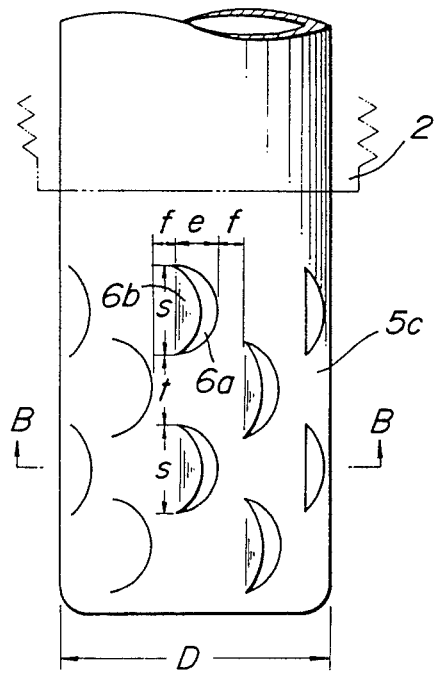

We claim:
1. An oxygen sensor with heater, comprising:
   a hollow electrolyte oxygen sensor element having a closed end and an open end;
   an inner and an outer electrode on the sensor element;
   a hollow ceramic heater, disposed within the sensor element and spaced therefrom, formed as a unitary body by sintering and embedding a metallized pat- tern ending with terminal patterns in a hollow, substantially cylindrical ceramic insulator;

a tubular insulator adjacent the open end of the sensor element;

a lead connected to the inner electrode and extending through the tubular insulator; and connecting terminals, extending within said tubular insulator, brazed to said terminal patterns of the ceramic heater to form brazed terminal portions; wherein the lead for the inner electrode and the brazed terminal portions are tightly secured by sealing with a heat-resistant ceramic bonding agent within said tubular insulator, and the hollow ceramic heater provides a communication passageway to the inside of the sensor element for a reference gas.

2. The sensor of claim 1, wherein said bonding agent is heat-resistant at a temperature higher than 700° C.

* * * * *

United States Patent [19]
Ebizawa et al.

[11] Patent Number: 4,507,192
[45] Date of Patent: Mar. 26, 1985

[54] OXYGEN SENSOR FOR EXHAUST GAS OF INTERNAL COMBUSTION ENGINE

[75] Inventors: Akio Ebizawa, Iwakura; Hisaharu Nishio, Tokai, both of Japan

[73] Assignee: NGK Spark Plug Co., Ltd., Nagoya, Japan

[21] Appl. No.: 569,936

[22] Filed: Jan. 12, 1984

Related U.S. Application Data

[63] Continuation of Ser. No. 342,815, Jan. 26, 1982, abandoned.

[30] Foreign Application Priority Data

Jun. 1, 1981 [JP] Japan .................................. 56-84668

[51] Int. Cl.³ ............................................ G01N 27/30
[52] U.S. Cl. .................................................... 204/428
[58] Field of Search ................ 204/1 S, 409, 410, 421, 204/424, 428

[56] References Cited

U.S. PATENT DOCUMENTS 4,065,372 12/1977 Hacker et al. .................... 204/195 S
4,184,934 1/1980 Bode et al. ....................... 204/195 S

FOREIGN PATENT DOCUMENTS 2326086 12/1974 Fed. Rep. of Germany .
2348505 4/1975 Fed. Rep. of Germany .
1469698 4/1975 United Kingdom .

Primary Examiner—John F. Niebling
Assistant Examiner—B. J. Boggs, Jr.
Attorney, Agent, or Firm—Fleit, Jacobson, Cohn & Price

[57] ABSTRACT

The oxygen sensor for exhaust gas of internal combustion engine includes a solid electrolyte tube having an inner electrode coated on the inner surface of said electrolyte tube outer electrode formed on outer surface of said electrolyte tube and disposed on the outside surface thereof so as to come in contact with exhaust gas and a metallic protective tube coaxially surrounding said electrode with a spacing therefrom. The sidewall of the protective tube has two similarly arranged matrices of holes, each hole being made by cutting an arcuate edge on the sidewall and bending the thus cut portion toward the inside of the protective tube, and the holes of one matrix are interposed among the holes of the other matrix while being offset therefrom in both the longitudinal and circumferential directions of the protective tube.

3 Claims, 4 Drawing Figures